United States Patent [19]

Baranski et al.

[11] Patent Number: 5,698,499
[45] Date of Patent: Dec. 16, 1997

[54] PHENOLIC BORATES AND LUBRICANTS CONTAINING SAME

[75] Inventors: John R. Baranski, Southington, Conn.; Cyril A. Migdal, Pleasant Valley, N.Y.

[73] Assignee: Uniroyal Chemical Company, Inc., Middlebury, Conn.

[21] Appl. No.: 794,110

[22] Filed: Feb. 3, 1997

[51] Int. Cl.$^6$ ............................................ C10M 139/00
[52] U.S. Cl. .................................. 508/198; 568/6
[58] Field of Search ........................ 508/198, 186, 508/199, 200; 568/1, 6; C10M 139/00

[56] References Cited

U.S. PATENT DOCUMENTS

| | | | |
|---|---|---|---|
| Re. 32,295 | 11/1986 | Braid et al. | |
| 3,347,793 | 10/1967 | Washburn | 508/200 |
| 4,328,113 | 5/1982 | Horodysky et al. | |
| 4,389,322 | 6/1983 | Horodysky . | |
| 4,507,216 | 3/1985 | Braid et al. | |
| 4,530,770 | 7/1985 | Braid | 508/200 |
| 4,698,169 | 10/1987 | Andress, Jr. et al. | |
| 5,252,237 | 10/1993 | Andress, Jr. et al. | |

FOREIGN PATENT DOCUMENTS 0 320 219   6/1989   European Pat. Off. .

*Primary Examiner*—Prince Willis, Jr.
*Assistant Examiner*—Cephia D. Toomer
*Attorney, Agent, or Firm*—Raymond D. Thompson

[57] ABSTRACT

A composition of matter having the structure

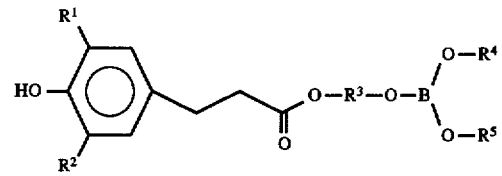

wherein $R^1$, $R^2$, $R^4$, and $R^5$ are independently a member selected from the group consisting of alkyl, cycloalkyl, aryl, aralkyl, and alkaryl, and $R^3$ is alkylene. Lubricants and lubricant additives comprising the composition are also disclosed. The lubricants are preferably lubricating oils.

56 Claims, No Drawings

PHENOLIC BORATES AND LUBRICANTS CONTAINING SAME

BACKGROUND OF THE INVENTION

1. Field of the Invention

This invention relates to lubricants. More particularly, the invention relates to a class of ashless, phosphorus-free, anti-fatigue, antiwear, extreme pressure, and friction modifying phenolic borate lubricant additives, preferably derived from boric acid, a primary alcohol, and an alkylhydroxy (3,5-di-alkyl{4-hydroxyphenyl}propionate).

2. Description of Related Art

In developing lubricating oils, there have been many attempts to provide additives that impart anti-fatigue, antiwear, and extreme pressure properties to the oils.

Zinc dialkyldithiophosphates (ZDDP) have been used in formulated oils as antiwear additives. However, zinc dialkyldithiophosphates produce ash, which contributes to particulate matter in automotive exhaust emissions. Regulatory agencies are seeking to reduce emissions of zinc into the environment. In addition, the phosphorus of these compounds is also suspected of limiting the service life of catalytic converters used on cars to reduce pollution. It is therefore important to limit the particulate matter and pollution formed during engine use for toxicological and environmental reasons, but it is also important to maintain the antiwear properties of the lubricating oil.

U.S. Pat. No. RE32,295 discloses that borate esters of hindered phenols are hydrolytically stable and possess antioxidant properties as fuel or lubricant additives.

U.S. Pat. No. 4,328,113 discloses borated amines as friction reducers in lubricating oils and lubricants.

U.S. Pat. No. 4,389,322 discloses the use of borated adducts of ethoxylated amides as a component of lubricating oils and greases.

U.S. Pat. No. 4,507,216 discloses that hindered phenyl esters of cyclic borates are useful in reducing the friction resulting when two surfaces are in sliding or rubbing contact.

U.S. Pat. No. 4,698,169 discloses products made by reacting an alkenyl succinic compound with an arylamine, an alkanolamine, a monoaminomethane, a hindered alcohol, and borated reaction products thereof, that are said to provide dispersant and antioxidant characteristics to lubricant compositions.

U.S. Pat. No. 5,252,237 discloses that alkoxy borates of alkylated phenols are effective cleanliness agents for lubricants and additives for improving the dropping point of greases.

One object of this invention is to provide novel phenolic borate compositions. Another object is to provide such phenolic borate compositions for use as ashless, phosphorus-free, anti-fatigue, antiwear, extreme pressure, and friction modifying lubricant additives.

SUMMARY OF THE INVENTION

The invention is a lubricant and, more particularly, a class of ashless, phosphorus-free, anti-fatigue, antiwear, extreme pressure, and friction modifying phenolic borate lubricant additives. Preferably, the invention is derived from boric acid, a primary alcohol, and an alkylhydroxy (3,5-dialkyl{4-hydroxyphenyl}propionate).

The invention relates to a composition of matter having the structure:

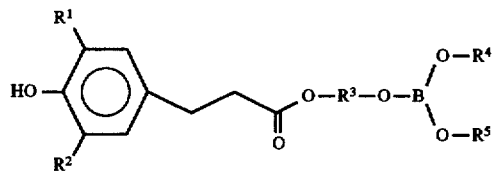

wherein $R^1$, $R^2$, $R^4$, and $R^5$ are independently a member selected from the group consisting of alkyl, cycloalkyl, aryl, aralkyl, and alkaryl; and $R^3$ is alkylene.

Another embodiment relates to a lubricant including a lubricant additive comprising a composition of matter having the structure:

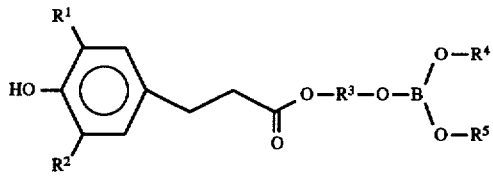

wherein $R^1$, $R^2$, $R^4$, and $R^5$ are independently a member selected from the group consisting of alkyl, cycloalkyl, aryl, aralkyl, and alkaryl; and $R^3$ is alkylene.

DESCRIPTION OF THE PREFERRED EMBODIMENTS

The additives of this invention can be used as either partial or complete replacements for the zinc dialkyldithiophosphates currently used. The additives of the invention can also be used in combination with other additives typically found in motor oils including other ashless antiwear additives. The typical additives found in motor oils are dispersants, detergents, rust inhibitors, antioxidants, antifoamants, friction modifiers, viscosity index (VI) improvers, and pour point depressants.

The class of ashless and phosphorus-free, anti-fatigue, antiwear, extreme pressure, and friction modifying phenolic borate lubricant additives of the present invention are of the following structure:

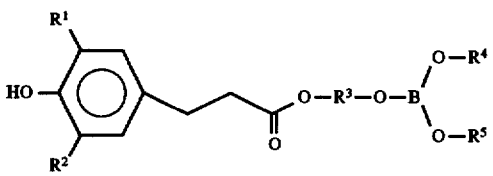

wherein $R^1$, $R^2$, $R^4$, and $R^5$ are independently a member selected from the group consisting of alkyl, cycloalkyl, aryl, aralkyl, and alkaryl; and $R^5$ is alkylene.

When $R^1$, $R^2$, $R^4$, and/or $R^5$ are alkyl, the substituents preferably comprise from 1 to 24 carbon atoms, more preferably from 2 to 12 carbon atoms, and most preferably from 4 to 10 carbon atoms. Thus, such alkyl groups have the structure $C_nH_{2n+1}$, where n is an integer, preferably an integer in the range of 1 to 12. Where such alkyl groups comprise three or more carbon atoms, the alkyl group can be either a straight chain or a branched chain. For example, $R^1$, $R^2$, $R^4$, and/or $R^5$ can be a member selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, and the like, and isomers thereof.

When $R^1$, $R^2$, $R^4$, and/or $R^5$ are cycloalkyl, the substituents preferably comprise from 3 to 12 carbon atoms, more preferably from 3 to 10 carbon atoms, and most preferably from 4 to 8 carbon atoms. Thus, such cycloalkyl groups have the structure $C_nH_{2n-1}$, where n is an integer, preferably an integer in the range of three to six. For example, $R^1$, $R^2$, $R^4$, and/or $R^5$ can be a member selected from the group consisting of cyclopropyl, cyclobutyl, cyclopentyl, cyclohexyl, cycloheptyl, cyclooctyl, and the like.

When $R^1$, $R^2$, $R^4$, and/or $R^5$ are aryl, aralkyl, or alkaryl, the substituents preferably comprise from 6 to 12 carbon atoms. Additionally, one or more of the ring carbon atoms can be replaced by an atom of a suitable alternative element, for example, nitrogen, oxygen, or sulfur. For example, $R^1$, $R^2$, $R^4$, and/or $R^5$ can be a residue of a member selected from the group consisting of benzene, toluene, xylene, indene, naphthalene, α-methylnaphthalene, β-methylnaphthalene, diphenyl, acenaphthene, fluorene, phananthrene, anthracene, fluoranthene, pyrene, chrysene, naphthacene, pyridine, picoline, quinoline, isoquinoline, quinaldine, indole, acridine, carbazole, hemimellitene, pseudocumene, mesitylene, prehnitene, isodurene, durene, pentamethylbenzene, hexamethylbenzene, ethylbenzene, propylbenzene, cumene, butylbenzene, cymene, triethylbenzene, hexaethylbenzene, styrene, α-methylstyrene, allylbenzene, stilbene, diphenylmethane, triphenylmethane, tetraphenylmethane, terphenyl, quaterphenyl, 1,3,5-triphenylbenzene, and the like. When $R^1$, $R^2$, $R^4$, and/or $R^5$ are aryl, the preferred substituent is a residue of benzene, i.e., a phenyl group.

It is preferred that $R^1$, $R^2$, $R^4$, and/or $R^5$ be a straight-chain or a branched-chain alkyl, more preferred that the substituents are a straight-chain or branched-chain lower alkyl, preferably lower alkyl of one to four carbon atoms, e.g. methyl, ethyl, propyl, butyl, and isomers thereof. It is most preferred that both $R^1$ and $R^2$ be t-butyl and that $R^4$ and $R^5$ both be n-butyl.

Those skilled in the art readily appreciate that the above described moieties, which can be employed as $R^1$, $R^2$, $R^4$, and $R^5$ in the practice of the invention, can have various substituents attached thereto, provided that such substituents do not adversely affect the utility of compositions as lubricant additives.

In the above structural formula, $R^3$ is an alkylene moiety, preferably an alkylene moiety of 1 to 12 carbon atoms, more preferably from 2 to 10 carbon atoms, most preferably from 2 to 6 carbon atoms. Thus, such an alkylene moiety has the structure $C_nH_{2n}$, where n is an integer, preferably an integer in the range of one to six. Such alkylene moieties can be either a straight chain or a branched chain. For example, $R^3$ can be a member selected from the group consisting of methylene (i.e., —$CH_2$—), ethylene (i.e., —$CH_2CH_2$—), propylene, butylene, pentylene, hexylene, heptylene, octylene, nonylene, decylene, and the like, and isomers thereof. It has been found especially advantageous for $R^3$ to be a 3-methypropylene moiety.

In a preferred embodiment, the phenolic borate derivatives of the invention are prepared by the interreaction of a primary alcohol, boric acid, and an alkylhydroxy (3,5-di-alkyl{4-hydroxyphenyl}propionate. Preferably, the invention is prepared with an alkylhydroxy (3,5-di-t-butyl{4-hydroxyphenyl}propionate.

The primary alcohol can, for example, be a member selected from the group consisting of methanol, ethanol, propanol, butanol, pentanol, hexanol, heptanol, octanol, nonanol, decanol, isomers of the foregoing compounds, mixtures thereof, and the like. The primary alcohol is preferably a lower alcohol, more preferably a lower alcohol having from one to four carbon atoms, e.g., methanol, ethanol, propanol, butanol, and isomers thereof. The most preferred alcohol is butanol, e.g., n-butanol.

The borating agent or boron-containing reagent of the invention is a member selected from the group consisting of boric acid, boron oxide, boron halide, and a boron acid ester. The preferred borating agent is boric acid.

The three alkyl groups of the alkylhydroxy (3,5-di-alkyl{4-hydroxyphenyl}propionate can each, individually, have from 1 to 24 carbon atoms and can be either a straight chain or a branched chain. For example, these alkyl groups can be independently a member selected from methyl, ethyl, propyl, butyl, pentyl, hexyl, heptyl, octyl, nonyl, decyl, isomers thereof, and the like. It is preferred that these alkyl groups be lower alkyl groups, for example, those having from one to four carbon atoms, such as, methyl, ethyl, propyl, butyl, and isomers thereof. It is more preferred that the alkyl group of the alkylhydroxy moiety of the alkylhydroxy (3,5-di-alkyl{4-hydroxyphenyl}propionate be 3-methylpropyl and most preferred that the di-alkyl moiety be di-t-butyl.

The additives of the present invention are especially useful as components in lubricating oil compositions. The additives can be included in a variety of oils with lubricating viscosity including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, metal-working lubricants, hydraulic fluids, and other lubricating oil and grease compositions. The additives can also be used in motor fuel compositions.

In general, the lubricant compositions of the invention contain the additives in a concentration ranging from about 0.1 to about 30 weight percent. A concentration range for the additives ranging from about 0.5 to about 15 weight percent based on the total weight of the oil composition is preferred. A preferred concentration range is from about 1.0 to about 7.5 weight percent. Oil concentrates of the additives can contain from about 1 to about 50 weight percent of the additive reaction product in a carrier or diluent oil of lubricating oil viscosity.

The additives of the invention can be used in lubricant compositions together with conventional lubricant additives. The typical additives found in lubricating oil compositions are dispersants, detergents, rust inhibitors, antioxidants, antifoamants, friction modifiers, viscosity index improvers, and pour point depressants.

The advantages and the important features of the present invention will be more apparent from the following examples.

EXAMPLE 1

This example illustrates the preparation of alkylhydroxy (3,5-di-t-butyl{4-hydroxyphenyl}propionate for use in the product of this invention.

A five-liter, four-neck, round-bottom flask was equipped with an overhead stirrer, a subsurface nitrogen sparge tube, a thermocouple probe, and a Graham condenser. The Graham condenser was fitted with a simple distillation head and a condenser. The vessel was charged with 1,880 grams of methyl 3-(3,5-di-t-butyl-4-hydroxyphenyl)propionate (commercially available from Uniroyal Chemical Company, Inc.), 3,090 milliliters of 1,3-butanediol, and 12.8 grams of p-toluene sulfonic acid monohydrate. The mole ratio of 1,3-butane diol to phenolic ester reactant was about 5.4:1. The system was purged with nitrogen, agitated, and warmed to 145° C. The system was held at 145° C. for 5.5 hours. The reaction mass was allowed to cool to about 80° C. and, thereafter, 750 milliliters of an Ashland Chemical Co. product of an aliphatic petroleum naphtha sold under the trademark Lacolene were added. The solution was initially extracted with 800 milliliters of 0.12M sodium bicarbonate and then extracted three times with 200 milliliter portions of water. Any remaining volatile matter was removed by rotary evaporation. The yield of light-colored, liquid product was 1,957 grams. The product obtained was a complex mixture of phenolic esters having a moderate viscosity at room temperature.

EXAMPLE 2

A quantity of 31.3 grams of the product of Example 1 and a quantity of 3.0 grams of boric acid were charged to a 100 milliliter, three-neck, round-bottom flask equipped with a thermocouple probe, an overhead stirrer, a 25 milliliter addition funnel, and a distillation head and condenser. An amount of 22 milliliters of dodecanol was charged to the addition funnel. The reactor contents were heated to 100° C. Water removal was facilitated using a moderate nitrogen purge. The temperature of 100° C. was held for 20 minutes and then increased to 130° C. and held for 30 minutes. The reaction was cooled to 100° C., and the dodecanol was added over five minutes. The temperature was maintained at 100° C. for 20 minutes and then raised to 150° C. This temperature was held for one hour. The reaction mixture was then cooled to 90° C., and the product was filtered through a coarse glass-fritted filter. An amount of 44.5 grams of a clear, pale-yellow liquid product was recovered.

EXAMPLE 3

An amount of 30.0 grams of the product of Example 1 and 3.97 grams of boric acid were charged to a 100 milliliter, three-neck, round-bottom flask equipped with a thermocouple probe, an overhead stirrer, and a distillation head and condenser. The reactor contents were heated to 100° C. Water removal was facilitated using a moderate nitrogen purge. The temperature of 100° C. was held for 20 minutes, then increased to 130° C., and held for 30 minutes. The reaction mixture was cooled to 100° C., and then 3.97 grams of boric acid, 5.79 grams of 1,3-butane diol, and 25.0 milliliters of 1-butanol were added to the reactor. The reactor contents were heated to 100° C. Water removal was facilitated using a slow nitrogen purge. The temperature was held at 100° C. for one hour. Then, the temperature was increased to 150° C. and held for one hour. The reactor contents were cooled to 50° C., and 75 milliliters of reagent hexanes were added. The product was filtered through a coarse glass-fritted filter. The volatiles were removed using a rotary evaporator. A quantity of 30.6 grams of a clear, pale-yellow, very thick liquid product were obtained.

EXAMPLE 4

An amount of 30.4 grams of the product of Example 1 and 4.02 grams of boric acid were charged to a 100 milliliter, three-neck, round-bottom flask equipped with a thermocouple probe, an overhead stirrer, and a distillation head and condenser. The reactor contents were heated to 100° C. Water removal was facilitated using a moderate nitrogen purge. The temperature was held at 100° C. for 20 minutes, then increased to 145° C., and held there for 30 minutes. The reaction mixture was cooled to 70° C., a quantity of 13 milliliters of 1-butanol was added, and the reaction mixture was heated to 100° C. Water removal was facilitated using a slow nitrogen purge. The temperature was held at 100° C. for one hour, increased to 150° C., and held for an additional hour. The reaction mixture was cooled to 50° C., and 40 milliliters of reagent hexanes were added. The product was filtered through a coarse glass-fritted filter. The volatiles were removed using a rotary evaporator. A quantity of 33.7 grams of a clear, pale-yellow liquid product of moderate viscosity was obtained.

EXAMPLE 5

This example compares additive products using a standard test.

The antiwear properties of the reaction product of this invention in a fully formulated lubricating oil were determined in the "Four-Ball Wear Test," described below, under the ASTM D 4172 test conditions. The fully formulated lubricating oils tested in this example also contained 1.0 weight percent cumene hydroperoxide to simulate the condition within a running engine. The additives were tested for effectiveness in two motor oil formulations, as described in Table 2, and compared to identical formulations with and without any zinc dialkyldithiophosphate. In Table 1 the numerical value of the test results (Average Wear Scar Diameter "mm") decreases with an increase in effectiveness. In many instances, antiwear additives are effective in lubricating oil containing no other additives. However, in fully formulated oils such additives may not perform well.

FOUR-BALL WEAR TEST

I. Purpose of Tests

The "Four-Ball Wear Test" evaluates the antiwear performance of oil and grease formulations and transportation fuels, such as diesel.

II. Apparatus

A Four-Ball Wear Test machine is used to perform this evaluation. Four balls are arranged in an equilateral tetrahedron. The lower three balls are clamped securely in a test cup filled with lubricant and the upper ball is held by a chuck that is motor-driven. The upper ball rotates against the fixed lower balls. Load is applied in an upward direction through a weight/lever arm system. Loading is through a continuously variable pneumatic loading system. Heaters allow operation at elevated oil temperatures.

The testing of this example was done on a Falex Variable Drive Four-Ball Wear Test Machine.

III. Test Procedures

The three stationary steel balls are immersed in 10 milliliters of sample to be tested, and the fourth steel ball is rotated on top of the three stationary balls in "point-to-point contact." The machine is operated for one hour at 75° C. with a load of 40 kilograms and a rotational speed of 1,200 revolutions per minute.

TABLE 1

Four-Ball Wear Results

| Compound | Formulation | Wear Scar Diameter "mm" |
| --- | --- | --- |
| Example 2 | A | 0.82 |
| Example 3 | A | 0.64 |

TABLE 1-continued

Four-Ball Wear Results

| Compound | Formulation | Wear Scar Diameter "mm" |
|---|---|---|
| Example 4 3-methylpropyl-3-{3,5-di-t-butyl (4-hydroxy-phenyl)propionyloxy} dibutyl borate | A | 0.57 |
| No antiwear additive | A | 0.93 |
| Zinc dialkyldithiophosphate | A | 0.46 |
| Example 4 3-methylpropyl-3-{3,5-di-t-butyl (4-hydroxy-phenyl)propionyloxy} dibutyl borate | B | 0.50 |
| No antiwear additive | B | 0.98 |
| Zinc dialkyldithiophosphate | B | 0.53 |

TABLE 2

| Formulation A | wt. % | Formulation B | wt. % |
|---|---|---|---|
| Solvent Neutral 100 | 22.8 | Solvent Neutral 100 | 22.8 |
| Solvent Neutral 150 | 60.0 | Solvent Neutral 150 | 60.0 |
| Succinimide Dispersant | 7.5 | Succinimide Dispersant | 7.5 |
| Overbased Calcium Phenate Detergent | 2.0 | Overbased Calcium Sulfonate Detergent | 2.0 |
| Neutral Calcium Sulfonate Detergent | 0.5 | Neutral Calcium Sulfonate Detergent | 0.5 |
| Antioxidant | 0.5 | Antioxidant | 0.5 |
| Rust Inhibitor | 0.1 | Rust Inhibitor | 0.1 |
| Pour Point Depressant | 0.1 | Pour Point Depressant | 0.1 |
| OCP VI Improver | 5.5 | OCP VI Improver | 5.5 |
| Antiwear Additive[1] | 1.0 | Antiwear Additive | 1.0 |

[1]In the case of no antiwear additive in Table 1, the product sold under the trademark Solvent Neutral 150 is used in its place at 1.0 weight percent.

The invention has been described in detail with particular reference to preferred embodiments thereof, but it is understood that variations and modifications can be effected within the spirit and scope of the invention.

What is claimed is:

1. A composition of matter having the structure

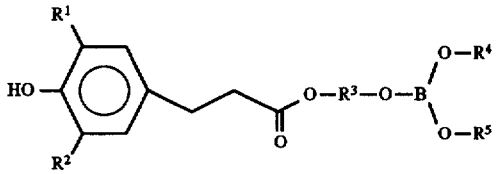

wherein $R^1$, $R^2$, $R^4$, and $R^5$ are independently a member selected from the group consisting of alkyl, cycloalkyl, aryl, aralkyl, and alkaryl, and $R^3$ is alkylene.

2. The composition of claim 1 wherein at least one of $R^1$, $R^2$, $R^4$, and $R^5$ is alkyl.

3. The composition of claim 2 wherein $R^1$, $R^2$, $R^4$, and $R^5$ are alkyl.

4. The composition of claim 2 wherein $R^1$ and $R^2$ are t-butyl.

5. The composition of claim 2 wherein $R^4$ and $R^5$ are n-butyl.

6. The composition of claim 4 wherein $R^4$ and $R^5$ are n-butyl.

7. The composition of claim 1 wherein $R^3$ is a lower alkylene group of one to four carbon atoms.

8. The composition of claim 2 wherein $R^3$ is a lower alkylene group of one to four carbon atoms.

9. The composition of claim 3 wherein $R^3$ is a lower alkylene group of one to four carbon atoms.

10. The composition of claim 4 wherein $R^3$ is a lower alkylene group of one to four carbon atoms.

11. The composition of claim 5 wherein $R^3$ is a lower alkylene group of one to four carbon atoms.

12. The composition of claim 6 wherein $R^3$ is a lower alkylene group of one to four carbon atoms.

13. The composition of claim 1 wherein $R^3$ is 3-methylpropylene.

14. The composition of claim 2 wherein $R^3$ is 3-methylpropylene.

15. The composition of claim 3 wherein $R^3$ is 3-methylpropylene.

16. The composition of claim 4 wherein $R^3$ is 3-methylpropylene.

17. The composition of claim 5 wherein $R^3$ is 3-methylpropylene.

18. The compositions of claim 1 wherein said composition is 3-methylpropyl-3-{3,5-di-t-butyl (4-hydroxyphenyl) propionyloxy}dibutyl borate.

19. A lubricant additive comprising a composition of matter having the structure wherein $R^1$, $R^2$, $R^4$, and $R^5$ are independently selected from the group consisting of alkyl, cycloalkyl, aryl, aralkyl, and alkaryl, and $R_3$ is alkylene.

20. The additive of claim 19 wherein the additive is a lubricating oil additive.

21. The additive of claim 19 wherein at least one of $R^1$, $R^2$, $R^4$, and $R^5$ is alkyl.

22. The additive of claim 21 wherein $R^1$, $R^2$, $R^4$, and $R^5$ are alkyl.

23. The additive of claim 21 wherein $R^1$ and $R^2$ are t-butyl.

24. The additive of claim 21 wherein $R^4$ and $R^5$ are n-butyl.

25. The additive of claim 23 wherein $R^4$ and $R^5$ are n-butyl.

26. The additive of claim 19 wherein $R^3$ is a lower alkylene group of one to four carbon atoms.

27. The additive of claim 21 wherein $R^3$ is a lower alkylene group of one to four carbon atoms.

28. The additive of claim 22 wherein $R^3$ is a lower alkylene group of one to four carbon atoms.

29. The additive of claim 23 wherein $R^3$ is a lower alkylene group of one to four carbon atoms.

30. The additive of claim 24 wherein $R^3$ is a lower alkylene group of one to four carbon atoms.

31. The additive of claim 25 wherein $R^3$ is a lower alkylene group of one to four carbon atoms.

32. The additive of claim 19 wherein $R^3$ is 3-methylpropylene.

33. The additive of claim 21 wherein $R^3$ is 3-methylpropylene.

34. The additive of claim 22 wherein $R^3$ is 3-methylpropylene.

35. The additive of claim 23 wherein $R^3$ is 3-methylpropylene.

36. The additive of claim 24 wherein $R^3$ is 3-methylpropylene.

37. The additive of claim 19 wherein said additive is 3-methylpropyl-3-{3,5-di-t-butyl(4-hydroxyphenyl) propionyloxy}dibutyl borate.

38. A lubricant comprising a lubricant additive comprising a composition of matter having the structure

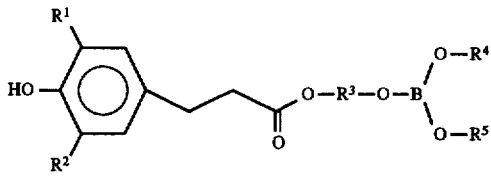

wherein $R^1$, $R^2$, $R^4$, and $R^5$ are independently a member selected from the group consisting of alkyl, cycloalkyl, aryl, aralkyl, and alkaryl, and $R^3$ is alkylene.

39. The lubricant of claim 38 wherein said lubricant is a lubricating oil.

40. The lubricant of claim 38 wherein at least one of $R^1$, $R^2$, $R^4$, and $R^5$ is alkyl.

41. The lubricant of claim 40 wherein $R^1$, $R^2$, $R^4$, and $R^5$ are alkyl.

42. The lubricant of claim 40 wherein $R^1$ and $R^2$ are t-butyl.

43. The lubricant of claim 40 wherein $R^4$ and $R^5$ are n-butyl.

44. The lubricant of claim 42 wherein $R^4$ and $R^5$ are n-butyl.

45. The lubricant of claim 38 wherein $R^3$ is a lower alkylene group of one to four carbon atoms.

46. The lubricant of claim 40 wherein $R^3$ is a lower alkylene group of one to four carbon atoms.

47. The lubricant of claim 41 wherein $R^3$ is a lower alkylene group of one to four carbon atoms.

48. The lubricant of claim 42 wherein $R^3$ is a lower alkylene group of one to four carbon atoms.

49. The lubricant of claim 43 wherein $R^3$ is a lower alkylene group of one to four carbon atoms.

50. The lubricant of claim 44 wherein $R^3$ is a lower alkylene group of one to four carbon atoms.

51. The lubricant of claim 38 wherein $R^3$ is 3-methylpropylene.

52. The lubricant of claim 40 wherein $R^3$ is 3-methylpropylene.

53. The lubricant of claim 41 wherein $R^3$ is 3-methylpropylene.

54. The lubricant of claim 42 wherein $R^3$ is 3-methylpropylene.

55. The lubricant of claim 43 wherein $R^3$ is 3-methylpropylene.

56. The lubricant of claim 38 wherein said additive is, 3-methylpropyl-3-{3,5-di-t-butyl(4-hydroxyphenyl) propionyloxy}dibutyl borate.

* * * * *